United States Patent [19]

Rau

[11] Patent Number: 4,998,537

[45] Date of Patent: Mar. 12, 1991

[54] SUPPORT FOR THE ANKLE JOINT AREA

[75] Inventor: Roland Rau, Gengenbach, Fed. Rep. of Germany

[73] Assignee: Deutsche Sporflex GmbH, Nurtingen, Fed. Rep. of Germany

[21] Appl. No.: 224,748

[22] Filed: Jul. 27, 1988

[51] Int. Cl.⁵ .................................. A61F 3/00
[52] U.S. Cl. ............................ 128/80 H; 128/166
[58] Field of Search ............... 128/80 H, 166, 602, 128/581–585, 610, 619, 596, 589, 591

[56] References Cited

U.S. PATENT DOCUMENTS

| | | | |
|---|---|---|---|
| 2,523,449 | 9/1950 | Rosenzweig | 128/581 |
| 3,067,531 | 12/1962 | Scott et al. | 128/581 |
| 3,527,211 | 9/1970 | Baker | 128/166 |
| 3,814,088 | 6/1974 | Raymond | 128/80 H |
| 4,084,586 | 4/1978 | Hettick | 128/80 H |
| 4,237,874 | 9/1989 | Nelson | 128/80 H |
| 4,280,488 | 7/1981 | Polsky et al. | 128/80 |
| 4,313,433 | 2/1982 | Cramer | 128/166 |
| 4,323,058 | 4/1982 | Detty | 128/80 H |
| 4,440,158 | 4/1984 | Shapiro | 128/80 H |
| 4,454,871 | 6/1984 | Mann et al. | 128/80 H |
| 4,502,470 | 3/1985 | Kiser et al. | 128/582 |
| 4,513,520 | 4/1985 | Koch | 128/80 H |
| 4,527,556 | 7/1985 | Nelson | 128/166 |
| 4,590,932 | 5/1986 | Wilkerson | 128/80 H |
| 4,724,847 | 2/1988 | Nelson | 128/80 H |
| 4,727,863 | 3/1988 | Nelson | 128/80 H |

FOREIGN PATENT DOCUMENTS

| | | | |
|---|---|---|---|
| 0275543 | 7/1988 | European Pat. Off. | 128/80 H |
| 8617783.4 | 2/1987 | Fed. Rep. of Germany | |
| 8617783.4 | 2/1987 | Fed. Rep. of Germany | |
| 2167964A | 6/1986 | United Kingdom | |

Primary Examiner—Edgar S. Burr
Assistant Examiner—Huong Q. Pham
Attorney, Agent, or Firm—Dick and Harris

[57] ABSTRACT

A supporting part in the form of a boot-like partial shoe, made of substantially rigid material, and which is open at the front and laterally encloses the rear area of the foot and also a portion of the lower part of the leg, with an opening in the supporting part at least in the area of an anklebone and fastener elements beside the front opening. The front area of the partial shoe located between the front edge and the opening for the anklebone is interrupted and substantially forms two tabs which overlap at their end portions. Swivel joints are operably arranged between the substantially overlapping end areas of the two tabs for enabling restrained relative motion between the substantially overlapping end portions of the two tabs. The interruption in the front area of the partial shoe ensures elimination of compressive and tensile stresses on the front area when the support is being worn and particularly when the wearer is walking. Therefore, fractures as a result of material fatigue are practically excluded. Arrangement of the fastener elements in the form of hook and loop fastaeners near top and sole regions of the supporting part, in the proximity of the front edge of the partial shoe enables particularly simple attachment of the support by an elaastic band without impeding the balancing movement in the front area of the partial shoe.

17 Claims, 3 Drawing Sheets

SUPPORT FOR THE ANKLE JOINT AREA

SUMMARY OF THE INVENTION

The invention relates to a support for the ankle joint area, in particular, for laterally supporting the lower ankle joint. The support comprises a supporting upper part in the form of a boot-like partial shoe made of substantially rigid material which is open at the front and laterally encloses the rear area of the foot and also a portion of the lower part of the leg. The supporting upper part has an opening at least in the area of an anklebone and fastener elements beside the front opening.

It is known to apply a support in the case of injuries in the ankle joint area in order to provide lateral support and hence immobilize the lower ankle joint. The known support is of a stirrup or U-shaped configuration with the ends which rest against the side of the lower part of the leg having to be secured by a bandage. The supporting forces which are converted into opposed thrust forces in the ends of the support must be absorbed by the bandage, and, therefore, the bandage must be wound relatively tightly. This adversely affects good blood circulation and is uncomfortable. In addition, application of the support is tedious and requires considerable specialized skill. Also, material fatigue occurs as a result of the supporting forces and often causes fractures in the support.

An object of the invention is to provide a support of the kind mentioned hereinabove with increased durability and improved lateral supporting stability which, at the same time, is easy to apply and simple to manufacture.

This and other objects of the invention will become apparent in light of the present specification, drawings and claims.

SUMMARY OF THE INVENTION

The objects of the invention are accomplished in a support apparatus for the lateral support of the lower ankle joint having a supporting part in the shape of a boot-like partial shoe, and constructed of a substantially rigid material. In the preferred embodiment of the invention, the supporting upper part has an open front, and laterally encloses the rear area of the foot and a portion of the lower part of the leg. An opening is provided in the supporting upper part in the region of the anklebone. Fastener elements are disposed adjacent the front opening of the supporting upper part. A front area of the supporting part, between its front edge and the opening in the region of the anklebone, is interrupted and substantially forms two tabs overlapping at their ends. Connection means are operably arranged between the substantially overlapping end areas of the two tabs for enabling restrained relative motion between the substantially overlapping end areas of the two tabs. The interruption ensures that compressive and tensile stresses on the front part of the support, in particular, during walking motions, are reduced and hence fractures due to material fatigue are substantially reduced.

In a preferred embodiment of the invention, the tabs are joined together so as to enable motion of the ends of the tabs relative to each other. On the one hand, such a connection improves the stability of the support and, on the other hand, it prevents the tabs from being subjected to excessive stress.

A support is preferred in which the tabs are connected by a rivet arranged in the rearward third of the end areas of the tabs. The characteristic feature of such a connection is that it can be manufactured at low cost. In particular, upon the occurrence of compressive forces, the ends of the tabs swivel rearwardly in the direction towards the opening for the anklebones. This reduces the likelihood of fracture due to material fatigue.

The fastener elements of the support are preferably in the form of hook and loop fasteners which are arranged beside the front lengthwise opening in the partial shoe near the top portion and near the sole portion of the partial shoe. A support of such design is particularly easy to close by wrapping an elastic band around the support, with slippage of the band being excluded once it has been applied.

In a particularly advantageous further development of the invention, the supporting upper part has openings in the area of the anklebones and preferably also in the heel area, with these openings being spanned by at least the outer skin. On the one hand, bruises caused by pressure are thereby avoided in these sensitive areas, and, on the other hand, the outer skin and possibly also the inner skin spanning the openings provide a soft support for the tissue in this area and so help to prevent the formation of so-called "window-type" oedemas. It is expedient for the inventive support to be of such dimensions that the supporting part extends, on the one hand, approximately over the tarsal bone or approximately over half of the length of the foot and, on the other hand, as far as approximately 5 cm above the anklebone. This offers, in the desired way, good stabilization against turning-over at the sides, with comfortable walking motions and rolling of the foot still being possible.

DETAILED DESCRIPTION OF THE DRAWINGS

Figure 1:
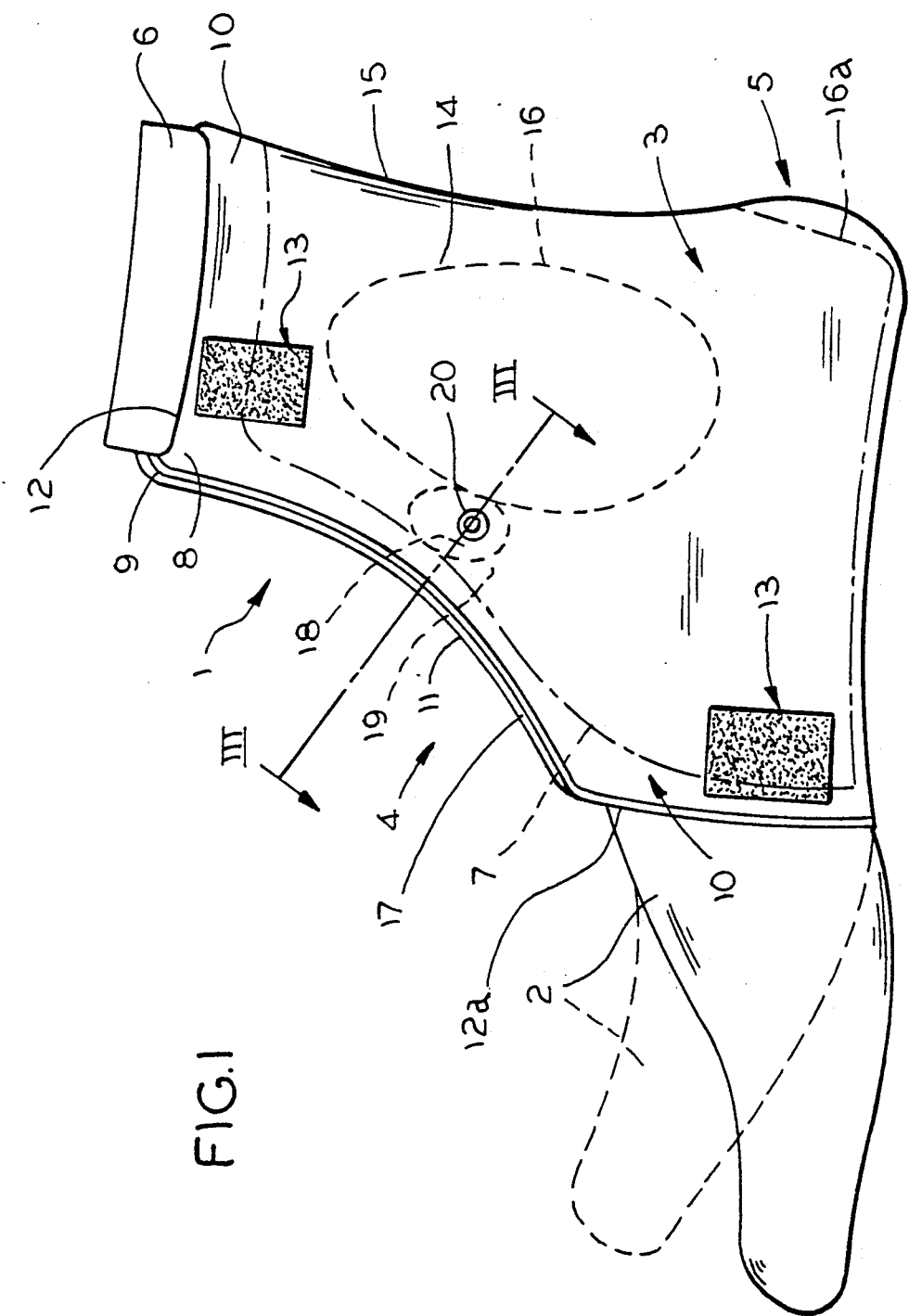
FIG. 1 is a left side elevation of a support according to the invention in its functioning state.

The support 1 shown in FIG. 1 serves to laterally support the lower ankle joint of a human foot 2. The support 1 is designed as partial shoe 3 which leaves approximately the front half of the foot exposed and encloses the tarsal area 4, the heel area 5 and also a portion of the lower part of the leg 6. This provides good support in the lateral direction. On the other hand, the wearer of the support 1 still has unrestricted walking freedom. The ability to move the foot as required for walking motions is indicated by a dashed line in the front area of the foot.

Partial shoe 3 has a supporting upper 7 consisting of a substantially rigid material, preferably a plastic material. The dot-and-dash line indicates where the outer edge of supporting upper part 7 extends within the partial shoe 3. Supporting upper part 7 is covered by an outer skin 8 and an inner skin 9 fabricated of, for example, thin imitation leather. Outer skin 8 and inner skin 9 extend beyond the edges of the supporting upper part 7. Outer skin 8 and the inner skin 9 are joined together, more particularly, adhesively, to form extension 10. The partial shoe is openable at the front and has fastener elements in the form of hook and loop fasteners 13 in the proximity of dividing area 11 at the top edge of the partial shoe and near the sole. On opening the hook and loop fasteners, the partial shoe 3 expands elastically to some extent in the dividing area 11, permitting partial shoe 3 to be slipped onto foot 2. In this way, the partial shoe 3 is easier to put on and also take off.

In spite of this elastic expandability of the partial shoe 3, there is a good stability in the lateral supporting direction because the side parts 14 of the supporting upper part 7 are integrally joined at the rear. Therefore, when the support 1 is subjected to stress at the sides, the forces are transferred through rear connection 15, with the side parts 14 stabilizing each other accordingly. In principle, rear connection 15 at the rear assumes the function of a wrapping strap required in a known support for a joint. Since this is not needed in the inventive support 1 it is significantly easier to put on and take off the support 1. All that is required to put on and take off the support is simply to open and close the hook and loop fasteners 13.

The partial shoe 3 according to the invention is preferably of thin-walled configuration. The resulting minimal bulk enables it to be worn inside a conventional shoe. Without the stabilization of the side parts 14 by the rear connection 15, the minimal bulk of partial shoe 3 would not be possible. Additionally, a support sole (not shown) may be affixed to the bottom of supporting upper part 7 to enable use of support 1 as a walking aid.

To enhance comfort during prolonged wear, it is extremely important for the supporting upper part 7 to have openings 16 and 16a in the area of the anklebones, and heel, respectively. Openings 16, 16a eliminate undesired compressive stress in these foot areas. Outer skin 8 spans these areas, as also may inner skin 9, thereby preventing them from being subjected to the comparatively hard supporting upper part 7, but still giving them support. This also eliminates so-called "window-type" oedemas.

As is clearly apparent from the preferred embodiment of the invention, as shown in FIG. 1, the front area of the support, extending between its front edge 17 and the opening 16 for the anklebone, is interrupted. A top tab 18 and a bottom tab 19 are both seen in this illustration. The top tab 18 extends over the bottom tab 19. Such an interruption in the front area of the support substantially eliminates compressive and tensile stresses such as occur particularly during walking motions when the support is being worn. Forward walking motion results in displacement of the top tab 18 in relation to the bottom tab 19.

A swivel joint produced by a rivet 20 is provided to enable defined and constrained motion of top tab 18 and bottom tab 19 relative to each other. As shown in FIG. 1, rivet 20 is positioned in the rearward third of the front area of supporting upper part 7, i.e., in the direction towards opening 16.

Such a swivel joint ensures defined and constrained motion of the front area of supporting upper part 7 during walking. If the angle between the foot 2 and the lower part 6 of the leg decreases as in a forward walking motion, and top portion 12 of supporting upper part 7 is forced toward toe portion 12a of supporting upper part 7, then the compressive force will cause the top tab 18 to swivel rearwardly together with the bottom tab 19 in the direction towards opening 16, the ends of top tab 18 and bottom tab 19 rotating about rivet 20. In this manner, compressive forces running from top portion 12 towards toe portion 12a, which would tend to buckle the front area of the supporting upper 7, if it were not interrupted, are instead deflected and absorbed by the relative rotational motion of the ends of top tab 18 and bottom tab 19. The deflection of compressive forces will tend to eliminate excessive stresses and, consequently, fractures, in the front area due to eliminate excessive stresses and, consequently, fractures in the front area due to material fatigue.

Instead of the swivel joint, it is, for example, also possible, in an alternative preferred embodiment of the invention to provide on the bottom tab 19, a short extension (not shown) which slides in a recess or guide in the top tab 18 while the two tabs swivel rearwardly in the direction towards the opening 16 during walking motion.

It therefore follows, that in particular, compressive forces are diminished solely by the interruption in the front area of the support. To avoid an undesired reduction in the lateral stability of the support, the tabs 18 and 19 are connected such that rotational motion of the tabs relative to each other is not excluded, but forces occurring in the front area can be transferred.

The fastener elements 13 serving to secure the support 1 are arranged on the support 1 such that the motion enabled by the interruption in the front area and by the joint is not impeded. Accordingly, preferably two fastener elements in the form of hook and loop fasteners 13 are arranged on each side of the support, of which only the hook and loop fasteners on one side of dividing area 11 are shown in FIG. 1. The first hook and loop fastener is positioned near the front edge 17 near the top portion 12 of supporting upper 7, adjacent lower leg 6. The second hook and loop fastener is positioned near the front edge 17 near the sole portion 12a of supporting upper 7. The placement of hook and loop fasteners 13 enables very simple attachment of an optional support sole. This further enables very simple attachment of the support to the foot using an elastic band.

Figure 2:
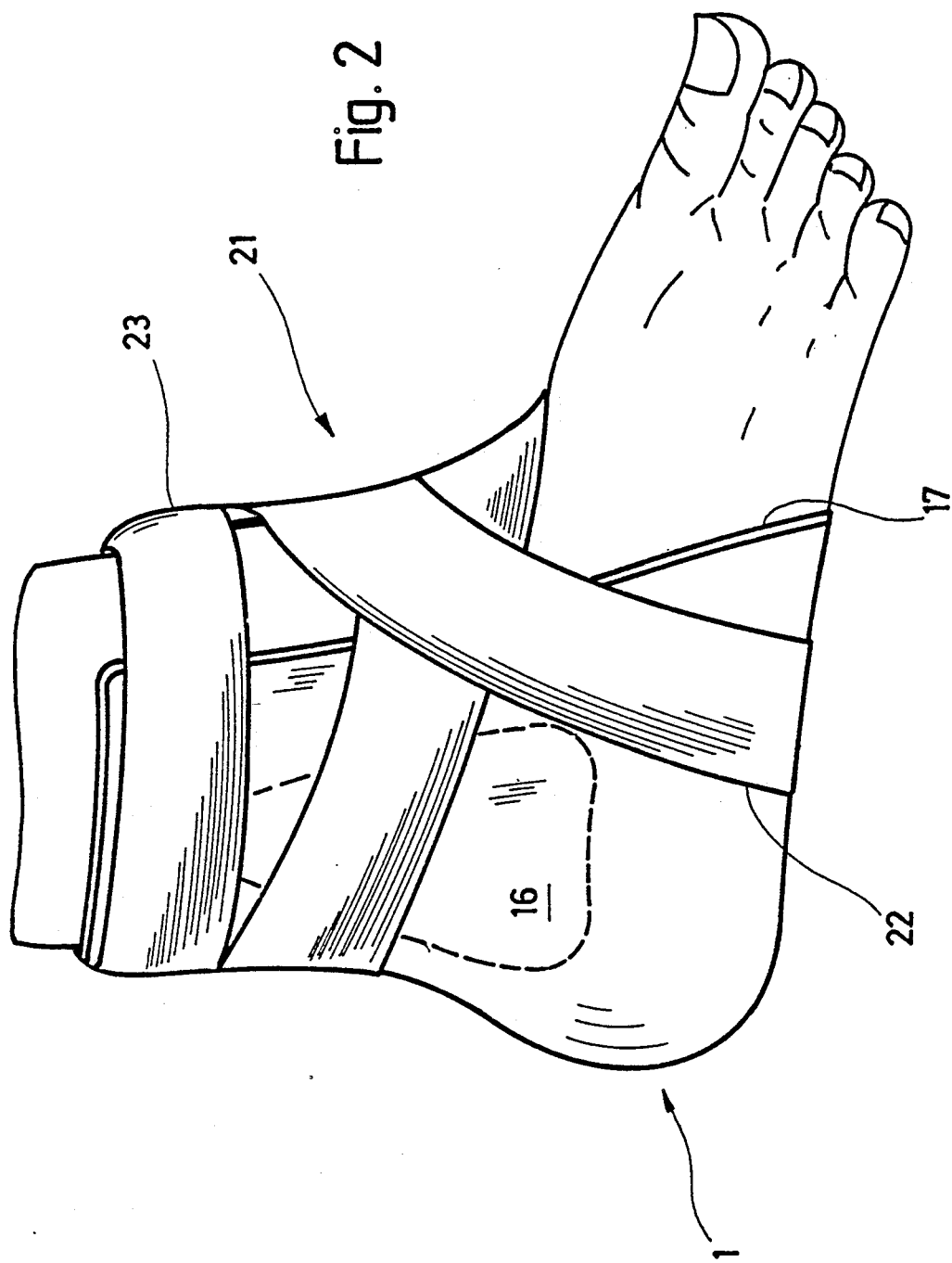
FIG. 2 is a right side perspective view of a support according to FIG. 2 secured by means of an elastic band.

FIG. 2 shows a sketch of a support 1 on a foot. It is secured by an elastic band 21 wrapped around the foot in the form of a figure-eight. The area 22 of the band extending upwardly from the sole of the foot is held firmly by the hook and loop fastener provided at that point. Immediately above the foot, i.e., in the area of the rivet 20 (not shown), the crossover prevents the band from slipping down. The area 23 of the band surrounding the upper of the support 1 is held firmly by the hook and loop fasteners at that point, thereby eliminating slippage.

Figure 3:
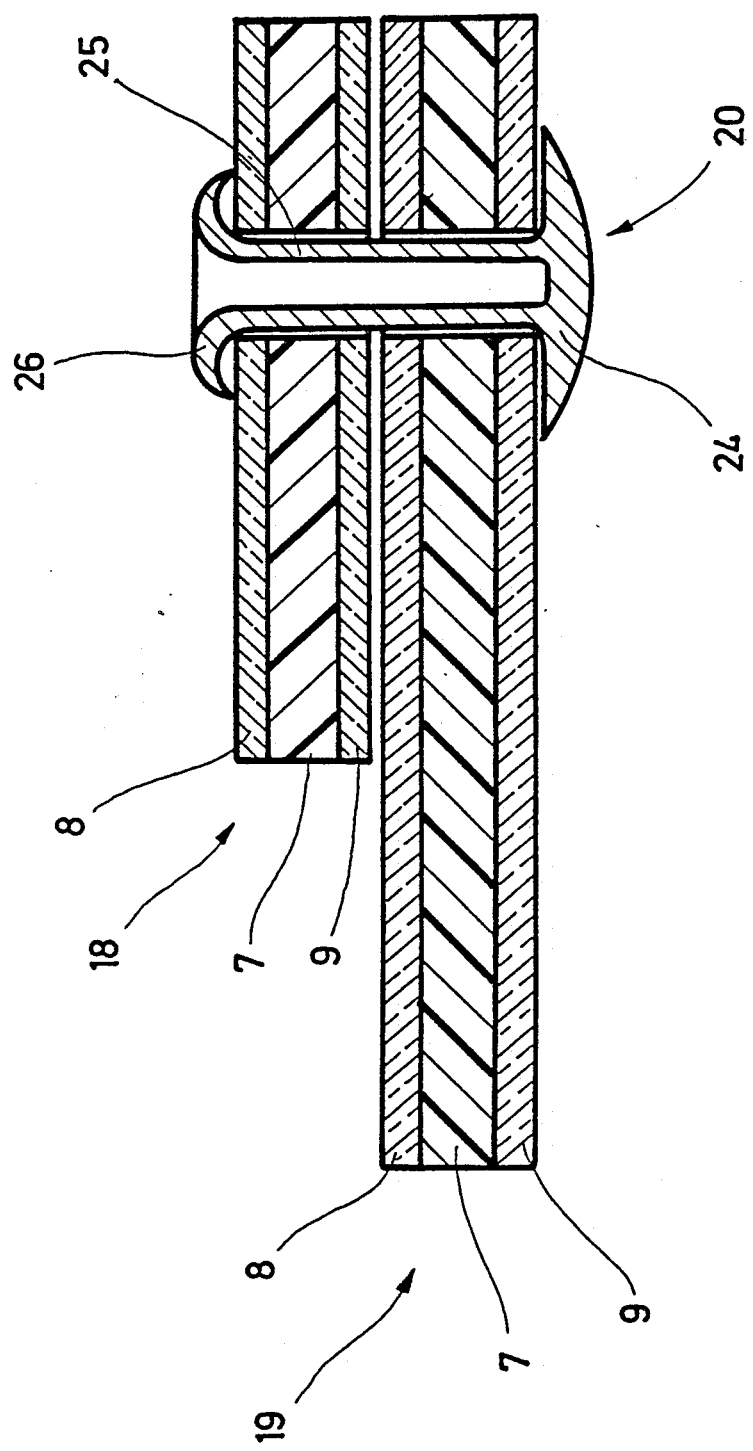
FIG. 3 is a schematic sectional view through the joint connection in the front area of the support taken along line III—III of FIG. 1.

FIG. 3 shows in more detail the joint connection made by a rivet 20 between the top tab 18 and the bottom tab 19 in the front area of the support 1. In the illustration, the top tab 18 is located over the bottom tab 19. The tabs 18, 19 are joined together by the rivet 20 which may, for example, take the form of a hollow rivet. The head 24 of the rivet 20 is as flat as possible so as to prevent bruises caused by pressure on the wearer's foot. Bruises due to pressure may also be obviated by the head being disposed in a recess (not shown) in the bottom tab 19.

The shaft 25 of the rivet is inserted through two holes in alignment with each other in the top tab 18 and the bottom tab 19. The end 26 of the rivet 20 opposite the head 24 is suitably bent to ensure that the two tabs are safely held together.

As shown clearly in the drawings, the support 1, i.e., its supporting upper part 7, extends over approximately half of the length of the foot and so the front area of the foot is not restricted from walking movements. The supporting upper part 7 extends upwardly in a boot-like manner beyond the anklebone area. Supporting upper 7 may extend beyond the anklebone area by, for example, approximately 5 centimeters. The total height of the support 1 from the sole of the foot to the top end is then between approximately 12 and 20 centimeters.

The support 1 according to the invention may be manufactured in different sizes, preferably for specific foot size ranges so as to eliminate the need for excessive adjustment of the support 1.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A support apparatus for an ankle joint area of a leg, in particular for laterally supporting a lower ankle joint, said support apparatus comprising:
   a supporting upper part having a boot-like partial shoe configuration for laterally enclosing a rear area of a foot and portions of the lower part of said leg,
   said supporting upper part being fabricated of substantially rigid material,
   said supporting upper part having front portions forming opposed sides defining a front opening, said front opening having at least one front edge,
   said supporting upper part further including at least one side opening in the area of an anklebone,
   at least one front area of said supporting upper part, between said at least one front edge and said at least one side opening on a common side of said supporting upper part being interrupted and formed as two tabs, which are overlapping,
   fastener means operably arranged adjacent said front opening for facilitating attachment of said support apparatus upon said ankle joint area, and
   a swivel joint member operably arranged adjacent said overlapping tabs for connecting said tabs and enabling relative motion between said overlapping tabs.

2. The apparatus according to claim 1 wherein said swivel joint member is operably arranged in a rearward third portion of said two tabs.

3. The apparatus according to claim 2 wherein said swivel joint member further comprises a rivet.

4. The apparatus according to claim 1 wherein said fastener means comprise:
   hook and loop fasteners operably arranged adjacent said front opening, proximate to a top region of said supporting upper part and adjacent a sole region of said supporting upper part.

5. The apparatus according to claim 4 wherein said fastener means are operably positioned upon substantially opposed sides of said front portions adjacent said front opening.

6. The apparatus according to claim 1 wherein said supporting upper part further includes a portion having a back opening for accommodating the heel towards reducing potential bruising or abrasion of said heel.

7. The apparatus according to claim 1 wherein, said apparatus further comprises:
   an elastically resilient layer operably arranged upon and extending substantially over an inner surface of said supporting part, for cushioning and protecting said foot.

8. The apparatus according to claim 7, wherein said elastically resilient layer further comprises:
   a layer of foamed material having a thickness of two millimeters.

9. The apparatus according to claim 1 wherein said apparatus further comprises:
   an outer skin operably arranged upon, and substantially covering, an outer surface of said supporting upper part.

10. The apparatus according to claim 9 wherein said outer skin further substantially extends across said at least one side opening.

11. The apparatus according to claim 10 further comprising:
    an elastically resilient layer operably arranged upon and extending substantially over an inner surface of said supporting upper part, for cushioning and protecting said foot;
    edge regions on said supporting upper part;
    at least said outer skin being arranged upon said supporting upper part so as to extend substantially outwardly beyond the edge regions of said supporting upper part,
    said outer skin and said elastically resilient layer being adhesively affixed to each other along corresponding peripheral regions thereof, adjacent said edge regions of said supporting upper part, for enclosing said supporting upper part.

12. The apparatus according to claim 11 wherein said supporting upper part extends for substantially half the length of the foot, from a heel region of said foot to a position proximate a tarsal bone region of said foot,
    said supporting upper part further extending substantially from a sole region of said foot to a position approximately five centimeters above said anklebone.

13. The apparatus according to claim 1 wherein said apparatus is configured for use within a person's conventional shoe as an inner shoe support.

14. The apparatus according to claim 6 wherein said apparatus further comprises:
    an outer skin operably arranged upon, and substantially covering, an outer surface of said supporting upper part.

15. The apparatus according to claim 14 wherein said outer skin further substantially extends across said at least one side opening and said back opening.

16. The apparatus according to claim 15 and further comprising:
    an elastically resilient layer operably arranged upon and extending substantially over an inner surface of said supporting upper part, for cushioning and protecting said foot;
    edge regions on said supporting upper part;
    at least said outer skin being arranged upon said supporting upper part so as to extend substantially outwardly beyond edge regions of said supporting upper part,
    said outer skin and said elastically resilient layer being adhesively affixed to each other along corresponding peripheral regions thereof, adjacent said edge regions of said supporting upper part, for enclosing said supporting upper part.

17. The apparatus according to claim 16 wherein said supporting upper part extends for substantially half the length of the foot, from a heel region of said foot to a position proximate a tarsal bone region of said foot, said supporting upper part further extending substantially from a sole region of said foot to a position approximately five centimeters above said anklebone.

* * * * *

UNITED STATES PATENT AND TRADEMARK OFFICE
CERTIFICATE OF CORRECTION

PATENT NO. : 4,998,537

DATED : March 12, 1991

INVENTOR(S) : Roland Rau

It is certified that error appears in the above-identified patent and that said Letters Patent is hereby corrected as shown below:

In the Abstract of the Invention:

| | |
|---|---|
| Title Page, Line 20 | Delete "fastaeners" and instead insert --fasteners-- |
| Title Page, Line 23 | Delete "elaastic" and instead insert --elastic-- |
| Col. 1 Line 4 | Delete "SUMMARY" and instead insert --BACKGROUND-- |
| Col. 4 Line 4 | Delete "supporting upper 7" and instead insert --supporting upper part 7-- |
| Col. 4 Line 35 | Delete "supporting upper 7" and instead insert --supporting upper part 7-- |
| Col. 4 Line 38 | Delete "upper 7" and instead insert --upper part 7-- |
| Col. 5 Line 6 | Delete "upper 7" and instead insert --upper part 7-- |

UNITED STATES PATENT AND TRADEMARK OFFICE
CERTIFICATE OF CORRECTION

PATENT NO. : 4,998,537

DATED : March 12, 1991

INVENTOR(S) : Roland Rau

It is certified that error appears in the above-identified patent and that said Letters Patent is hereby corrected as shown below:

Col. 2 Line 60          Delete "supporting upper 7" and instead insert --supporting upper part 7--

Signed and Sealed this

Nineteenth Day of January, 1993

Attest:

DOUGLAS B. COMER

Attesting Officer      Acting Commissioner of Patents and Trademarks